US010722405B2

(12) United States Patent
Pepin et al.

(10) Patent No.: US 10,722,405 B2
(45) Date of Patent: Jul. 28, 2020

(54) SMART DIAPER FOR DETECTING AND DIFFERENTIATING FECES AND URINE

(71) Applicant: Verily Life Sciences LLC, Mountain View, CA (US)

(72) Inventors: Brian Pepin, San Francisco, CA (US); Huanfen Yao, Brisbane, CA (US)

(73) Assignee: VERILY LIFE SCIENCES LLC, South San Francisco, CA (US)

( * ) Notice: Subject to any disclaimer, the term of this patent is extended or adjusted under 35 U.S.C. 154(b) by 628 days.

(21) Appl. No.: 15/292,389

(22) Filed: Oct. 13, 2016

(65) Prior Publication Data

US 2018/0104114 A1 Apr. 19, 2018

(51) Int. Cl.
*A61F 13/15* (2006.01)
*A61F 13/42* (2006.01)
(Continued)

(52) U.S. Cl.
CPC .......... *A61F 13/42* (2013.01); *A61F 13/8405* (2013.01); *G01N 27/048* (2013.01);
(Continued)

(58) Field of Classification Search
CPC .................. A61F 13/42; A61F 13/8405; A61F 2013/421; A61F 2013/423;
(Continued)

(56) References Cited

U.S. PATENT DOCUMENTS

| 3,013,257 A | 12/1961 | Ippolito |
| 3,261,987 A | 7/1966 | Chapin |

(Continued)

FOREIGN PATENT DOCUMENTS

| CN | 205246547 | 5/2016 |
| CN | 106198538 | 12/2016 |

(Continued)

OTHER PUBLICATIONS

International Application No. PCT/US2017/055840, "International Search Report and Written Opinion", dated Nov. 27, 2017, 14 pages.

(Continued)

*Primary Examiner* — Jacqueline F Stephens
(74) *Attorney, Agent, or Firm* — Kilpatrick Townsend & Stockton LLP

(57) ABSTRACT

A diaper sensor for detecting and differentiating feces and urine in a diaper is described. The diaper sensor may include at least one pair of conductive elements positioned within an absorbent region of the diaper. The diaper sensor may also include a transmitter and a control circuit operatively connected to the at least one pair of conductive elements and the transmitter. The diaper sensor may further include a power source operatively connected to the control circuit. The control circuit may measure the conductivity between the at least one pair of conductive elements. The control circuit may also determine whether there is poop or pee present in the diaper using the conductivity. The control circuit may also transmit via the transmitter a signal indicative of whether there is excrement or pee present in the diaper.

15 Claims, 5 Drawing Sheets

(51) Int. Cl.
- *A61F 13/84* (2006.01)
- *G01N 27/04* (2006.01)
- *G01N 33/483* (2006.01)
- *G01N 33/493* (2006.01)

(52) U.S. Cl.
CPC ....... *G01N 33/4833* (2013.01); *G01N 33/493* (2013.01); *A61F 2013/421* (2013.01); *A61F 2013/423* (2013.01); *A61F 2013/424* (2013.01); *A61F 2013/8479* (2013.01)

(58) Field of Classification Search
CPC ....... A61F 2013/424; A61F 2013/8479; G01N 33/4833; G01N 33/493
USPC .................................................. 604/361, 362
See application file for complete search history.

(56) References Cited

U.S. PATENT DOCUMENTS

| | | | |
|---|---|---|---|
| 4,315,159 | A | 2/1982 | Niwa et al. |
| 5,079,541 | A | 1/1992 | Moody |
| 5,616,140 | A | 4/1997 | Prescott |
| 5,654,803 | A | 8/1997 | Howard, III et al. |
| 6,147,592 | A | 11/2000 | Ulrich et al. |
| 6,287,253 | B1 | 9/2001 | Ortega et al. |
| 8,111,165 | B2 | 2/2012 | Ortega et al. |
| 8,416,088 | B2 | 4/2013 | Ortega et al. |
| 8,628,506 | B2 | 1/2014 | Ales, III et al. |
| 8,920,332 | B2 | 12/2014 | Hong et al. |
| 2002/0026164 | A1 | 2/2002 | Camarero Roy et al. |
| 2004/0022053 | A1 | 2/2004 | Sharon et al. |
| 2005/0019508 | A1 | 1/2005 | Engel et al. |
| 2005/0195085 | A1 | 9/2005 | Cretu-petra |
| 2006/0244614 | A1* | 11/2006 | Long .................. A61F 13/42 340/573.5 |
| 2007/0142796 | A1* | 6/2007 | Mosbacher ......... A61F 13/42 604/361 |
| 2007/0142799 | A1* | 6/2007 | Ales ................... A61F 13/42 604/361 |
| 2008/0021429 | A1 | 1/2008 | Klofta et al. |
| 2009/0157025 | A1 | 6/2009 | Song et al. |
| 2009/0275908 | A1 | 11/2009 | Song |
| 2010/0290948 | A1 | 11/2010 | Song |
| 2012/0109087 | A1* | 5/2012 | Abraham ............ A61F 13/42 604/361 |
| 2012/0116337 | A1 | 5/2012 | Ales et al. |
| 2013/0066289 | A1 | 3/2013 | Song et al. |
| 2014/0143183 | A1 | 5/2014 | Sigal et al. |
| 2014/0200538 | A1* | 7/2014 | Euliano .............. A61F 13/42 604/361 |
| 2015/0164377 | A1 | 6/2015 | Nathan et al. |
| 2016/0287074 | A1 | 10/2016 | Pradeep et al. |
| 2016/0292576 | A1 | 10/2016 | Pradeep et al. |
| 2016/0292584 | A1 | 10/2016 | Weinberg et al. |
| 2017/0128274 | A1 | 5/2017 | Varga et al. |
| 2017/0215808 | A1 | 8/2017 | Shimol et al. |
| 2017/0252225 | A1 | 9/2017 | Arizti et al. |
| 2017/0348162 | A1 | 12/2017 | Arizti et al. |
| 2018/0253957 | A1 | 9/2018 | Jhangiani et al. |

FOREIGN PATENT DOCUMENTS

| | | |
|---|---|---|
| EP | 2832323 | 2/2015 |
| JP | 61296239 | 12/1986 |
| KR | 1020090041260 | 4/2009 |
| WO | 0100117 | 1/2001 |
| WO | 02063260 | 8/2002 |
| WO | 2007128038 | 11/2007 |
| WO | 2012059832 | 5/2012 |

OTHER PUBLICATIONS

U.S. Appl. No. 15/971,306, "Non-Final Office Action", dated Jan. 28, 2019, 12 pages.

Kastle et al., "A New Family of Sensors for Pulse Oximetry", Hewlett Packard Journal, vol. 48., 1997, pp. 1-17.

Kim et al., "Miniaturized Battery-Free Wireless Systems for Wearable Pulse Oximetryy", Advanced Functional Materials, vol. 27 No. 1, 1604373., Jan. 2017, pp. 1-18.

Leonard et al., "Standard Pulse Oximeters Can be Used to Monitor Respiratory Rate", Emergency Medicine Journal, vol. 20, No. 6, 2003, pp. 524-525.

International Application No. PCT/US2019/030684, "International Search Report and Written Opinion", dated Jun. 25, 2019, 11 pages.

U.S. Appl. No. 15/971,306, "Notice of Allowance", dated Oct. 22, 2019, 9 pages.

* cited by examiner

SMART DIAPER FOR DETECTING AND DIFFERENTIATING FECES AND URINE

TECHNICAL FIELD

The present disclosure relates generally to the field of diapers, and more particularly, smart diapers for detecting and differentiating solid and liquid waste.

BACKGROUND DESCRIPTION

Monitoring babies' diapers for solid (feces) and/or liquid waste (urine) is a perpetual task for caregivers. It is preferred to limit the time a baby is wearing a soiled diaper to reduce discomfort and reduce the likelihood of the baby developing skin rash and irritation (e.g., diaper rash), the primary cause of which is the prolonged wearing of soiled diapers before they are changed. In addition to babies, it is also preferred to limit the time other individuals (e.g., elderly, sick, disabled, mentally ill, etc.) wear soiled diapers. Existing diaper technology includes sensors integrated into the diaper that can sense wetness in a diaper and indicate the information to a caregiver in a variety of forms, including for example, a color-sensing strip, alarm, or by wirelessly notifying the caretaker via a smartphone or similar device. But, integrated diaper wetness sensors cannot differentiate between solid and liquid waste, which would provide enhanced functionality to caregivers who may have a different response depending on whether an individual has urinated or defecated. Sensing devices that separately determine whether urine or feces is present in a diaper have been developed, but they are large, expensive, reusable sensors that attach to the exterior of the diaper, which is inconvenient and less functional for use by caregivers. Accordingly, there is much room for significant advancement in the technology in order to lower the cost and enhance the convenience and functionality thus making them a more affordable and reliable option.

SUMMARY

In one aspect, the present disclosure is directed to a diaper sensor for detecting and differentiating feces and urine in a diaper. The diaper sensor may include at least one pair of conductive elements positioned within an absorbent region of the diaper. The diaper sensor may also include a transmitter and a control circuit operatively connected to the at least one pair of conductive elements and the transmitter. The diaper sensor may further include a power source operatively connected to the control circuit. The control circuit may measure the conductivity between the at least one pair of conductive elements. The control circuit may also determine whether there is feces or urine present in the diaper using the conductivity. The control circuit may also transmit via the transmitter a signal indicative of whether there is feces or urine present in the diaper.

In another aspect, the present disclosure is directed to a method of monitoring a diaper using a diaper sensor. The method may include measuring a conductivity between a pair of conductive elements of a diaper sensor, wherein the pair of conductive elements are positioned within an absorbent region of a diaper. The method may further include determining whether there is feces or urine present in the diaper based on the conductivity. The method may also include transmitting from the diaper sensor a signal indicative of whether there is feces or urine present in the diaper.

In another aspect, the present disclosure is directed to a diaper sensor for detecting and differentiating feces and urine in a diaper. The diaper sensor may include at least one pair of conductive elements positioned within an absorbent region of the diaper. The diaper sensor may also include a transmitter and a control circuit operatively connected to the at least one pair of conductive elements and the transmitter. The diaper sensor may also include a power source operatively connected to the control circuit. The control circuit may measure the conductivity between the at least one pair of conductive elements to determine an impedance. The control circuit may also determine whether there is feces or urine present in the diaper based on the impedance. The control circuit may further transmit via the transmitter a signal indicative of whether there is feces or urine present in the diaper.

DETAILED DESCRIPTION

Reference will now be made in detail to embodiments of the present disclosure, examples of which are illustrated in the accompanying drawings. Where possible, the same reference numbers will be used throughout the drawings to refer to the same or like parts.

Figure 1:
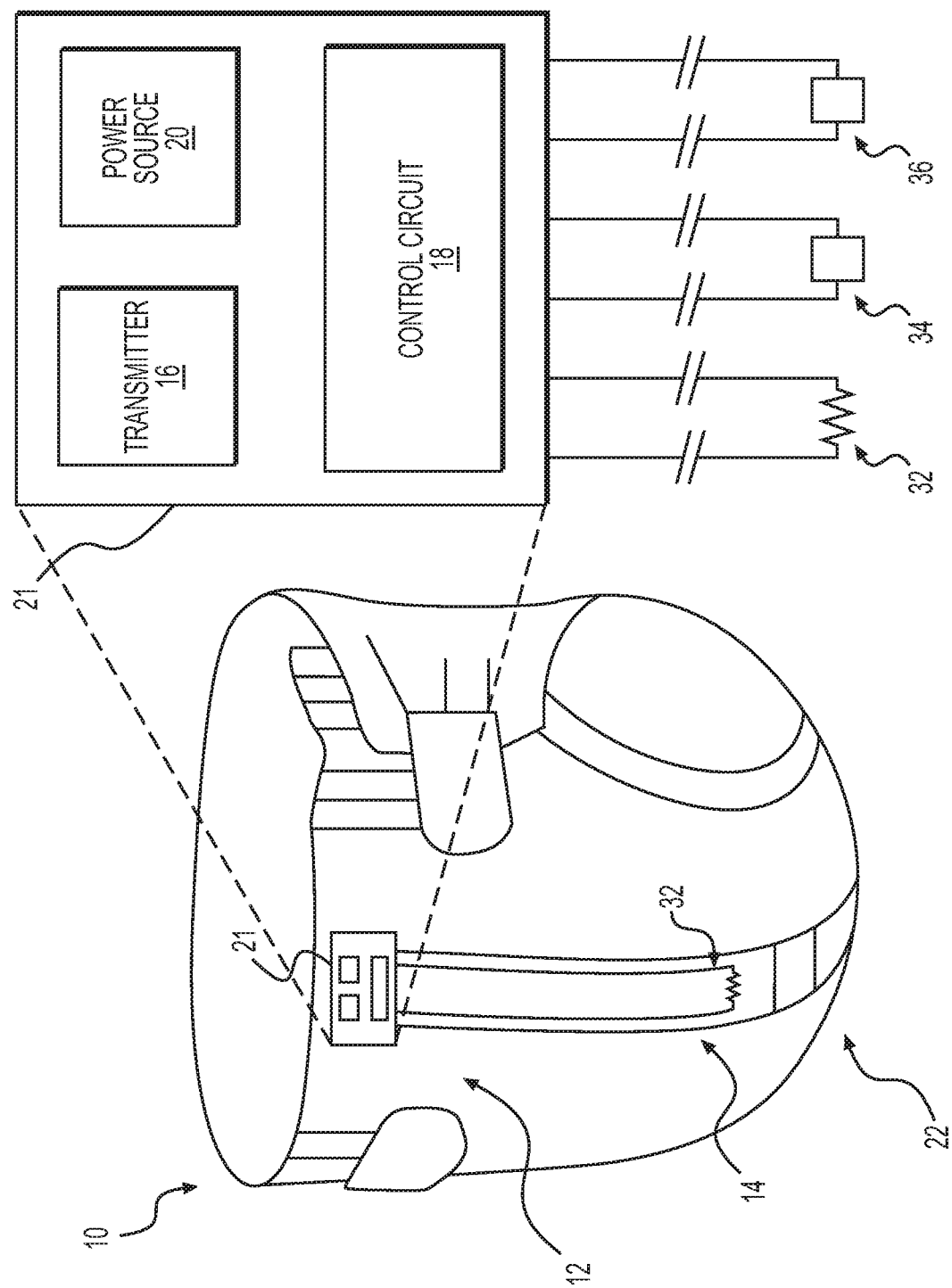
FIG. 1 is a perspective schematic of a diaper and diaper sensor, according to an exemplary embodiment.

FIG. 1 shows a perspective schematic view of a diaper 10, which includes a diaper sensor 12 designed to detect and differentiate between feces and urine in diaper 10. Diaper sensor 12 may include at least one pair of conductive elements 14 and a transmitter 16, a control circuit 18, and a power source 20 forming an electronics module 21.

Conductive elements 14 may be positioned within an absorbent region 22 of diaper 10 and may be configured to enable control circuit 18 to measure the conductivity between conductive elements 14 in order to determine an impedance and detect and differentiate feces and urine. Control circuit 18 may be designed or programmed with instructions to control the operation of diaper sensor 12, including for example, detecting and differentiating between feces and urine based on the impedance. Control circuit 18 may be operatively connected to conductive elements 14, transmitter 16, and power source 20. Transmitter 16 may be configured to wirelessly transmit a signal to a remote device (e.g., a smart phone, a smart watch, a computer, etc.) using one or more wireless communication methods. Power source 20 may be configured to power transmitter 16 and control circuit 18 and other electronic components and/or sensors. The different elements of diaper sensor 12 will now be discussed in further detail herein.

Figure 2:
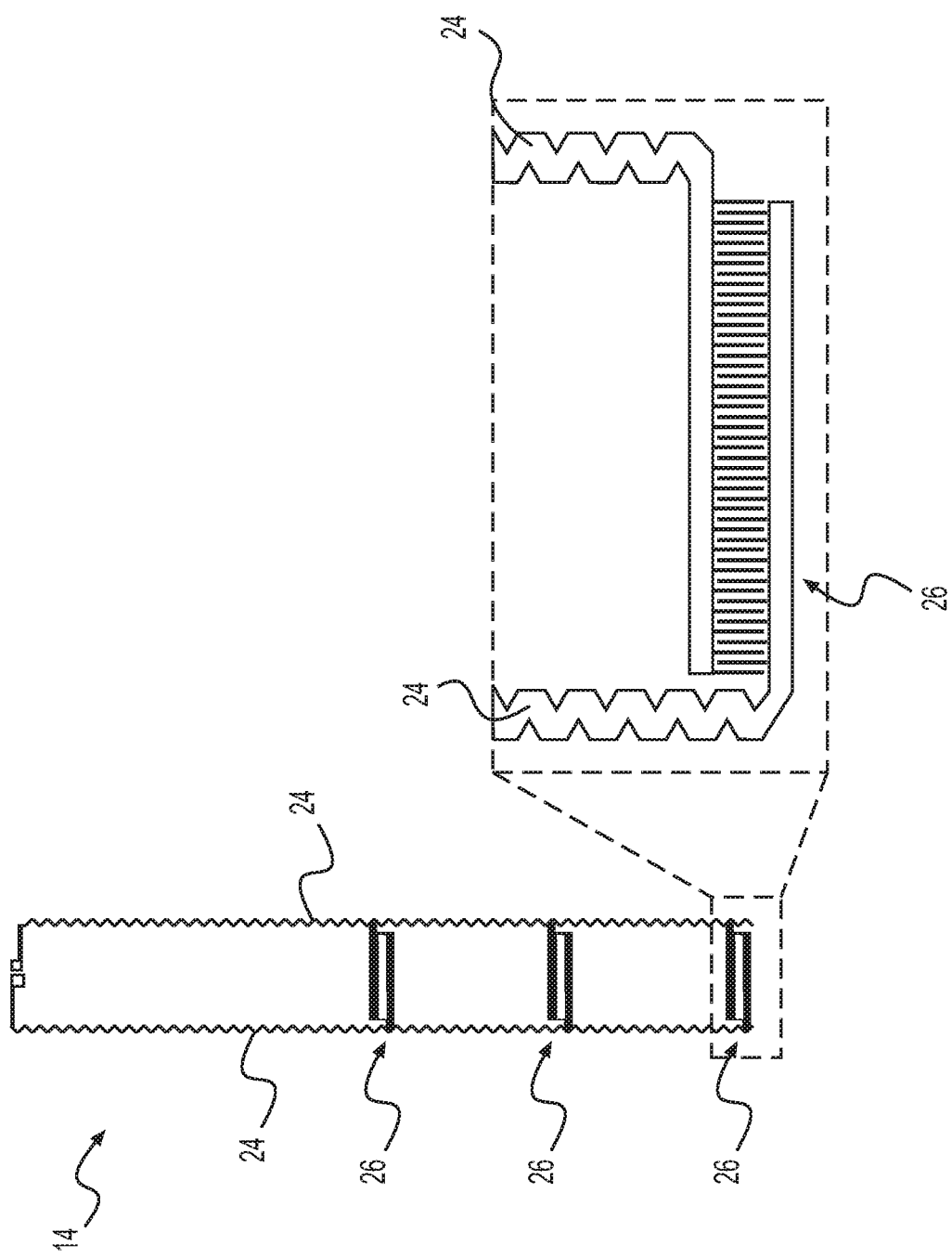
FIG. 2 is a schematic of conductive elements of the diaper sensor of FIG. 1.

Conductive elements 14 may extend from electronic module 21 to absorbent region 22 of diaper 10, as shown in FIG. 1. Absorbent region 22 may be defined as the region of the diaper designed to absorb liquid and moisture and absorbent region 22 may be positioned and extend to any and/or all regions of diaper 10 where feces or urine may be present. Conductive elements 14 may be formed of flexible conductive traces. In some embodiments, as shown in FIG. 2, at least a portion of conductive elements 14 may be formed of zig-zag conductive traces 24, which may expand and contract in length in response to expansion and contraction of diaper 10. In some embodiments, conductive elements 14 may include one or more sensing elements 26 formed between conductive traces 24. For example, FIG. 2 shows three sensing elements 26 positioned between conductive traces 24 and spaced apart in absorbent region 22. Each sensing element 26 may be formed of a plurality of microelectrodes connected to conductive traces 24, positioned in an interdigitated array, as shown in FIG. 2. In some embodiments, the microelectrodes may be formed of conductive fibers (e.g., carbon fibers). In some embodiments, conductive elements 14 including conductive traces 24 and/or sensing elements 26 may be woven directly into nonconductive fibers form absorbent region 22 of diaper 10.

The number and size of the microelectrodes forming the interdigitated array of sensing elements 26 may vary. In some embodiments, the number of microelectrodes of each sensing element 26 may range from, for example, 1 to 10, 10 to 20, 20 to 30, 30 to 40, 40 to 50, or more than 50. A width of the microelectrodes and a gap between the microelectrodes may also be varied. In some embodiments, the width of the microelectrodes may be, for example, about 50 µm, about 100 µm, about 150 µm, about 200 µm, about 250 µm, about 300 µm, about 350 µm, and about 400 µm. In some embodiments, the gap between the microelectrodes may be, for example, about 50 µm, about 100 µm, about 150 µm, about 200 µm, about 250 µm, about 300 µm, about 350 µm, and about 400 µm. The microelectrodes may be formed of any suitable conductive sensing material, including for example, gold, copper, platinum, and conductive polymers. The material of the microelectrodes may be a biocompatible or a non-toxic material. A total area of sensing elements 26 may also vary. For example, sensing elements 26 may have a total area about the size of a penny or may have a larger total area of several square inches.

In some embodiments, measuring the conductivity between opposing microelectrodes may be used to determine the substance of the material in between. For example, when the substance between the microelectrodes is substantially air the electrical conductivity may be about $3\times10^{-14}$ mS/cm to $8\times10^{-14}$ mS/cm at 20° C. When the substance between the microelectrodes is substantially urine the electrical conductivity may be about 100 mS/cm to about 300 mS/cm, about 120 mS/cm to about 200 mS/cm, about 140 mS/cm to about 180 mS/cm, or about 160 mS/cm. When the substance between the microelectrodes is substantially feces the electrical conductivity may be between the conductivity for air and urine. For example, the conductivity for feces may vary between about 1 and 50 mS/cm.

In some embodiments, the measured conductivity may be used to determine the impedance between the microelectrodes and the impedance may be used to determine the substance of the material in between opposing microelectrodes. The impedance may be determined based on the electrical conductivity and will vary based on the frequency. For example, the impedance of air at about 10 Hz may be between about $10^8$ and $10^9$ ohms ($\Omega$), at about 100 Hz may be about $10^8 \Omega$, at about 1 kHz may be about $10^8 \Omega$, at about 3 kHz may be between about $10^6$ to $10^7 \Omega$. The impedance of urine at about 10 Hz may be between about $10^5$ and $10^6 \Omega$, at about 100 Hz may be about $10^5 \Omega$, at about 1 kHz may be about $10^4 \Omega$, at about 3 kHz may be between about $10^3$ to $10^4 \Omega$. The impedance of feces at about 10 Hz may be between about $10^6$ and $10^7 \Omega$, at about 100 Hz may be between about $10^5$ to $10^6 \Omega$, at about 1 kHz may be between about $10^4$ and $10^5 \Omega$, at about 3 kHz may be between about $10^4$ to $10^5 \Omega$. The difference in the impedance of each substance (i.e., air, urine, and feces) at the different frequencies may enable determination of the substance. In other words, when the impedance is high there may no feces or urine present, when the impedance is low there may be urine present, when the impedance is between high and low then there may be feces present. In some embodiments, determination of the substance may be done based on the determined impedance at one or more frequencies.

Control circuit 18 may be any suitable type of circuit capable of measuring the conductivity between conductive elements 14, determining the impedance, and identify the substance based on the conductivity and/or the impedance. In some embodiments, control circuit 18 may be an application specific integrated circuit (ASIC). In some embodiments, control circuit 18 may be constructed of a microcontroller mounted to a printed circuit board assembly (PCBA). In some embodiments, transmitter 16 and power source 20 may also be mounted to the PCBA. The microcontroller may include one or more processors, including for example, a central processing unit (CPU). The processors may include any suitable type of commercially available processor or may be a custom design. Control circuit 18 may include additional components, for example, non-volatile memory (e.g., a flash memory), volatile memory (e.g., a random access memory (RAM)), and other like components, configured to store information).

Control circuit 18 may be constructed of a rigid circuit board, flex circuit board, or a combination of both (i.e., a rigid-flex circuit board). For example, a core of control circuit 18 may include a rigid circuit board portion and then flexible circuit board portions may extend out from the rigid circuit board portion. The flexible circuit board portions may be designed to fold or twist and include contacts enabling connection to other elements of diaper sensor 12 (e.g., conductive elements 14, transmitter 16, and power source 20).

Power source 20 may be any suitable type of power source, including for example, a battery, a capacitor, or other power storage device.

Figure 3:
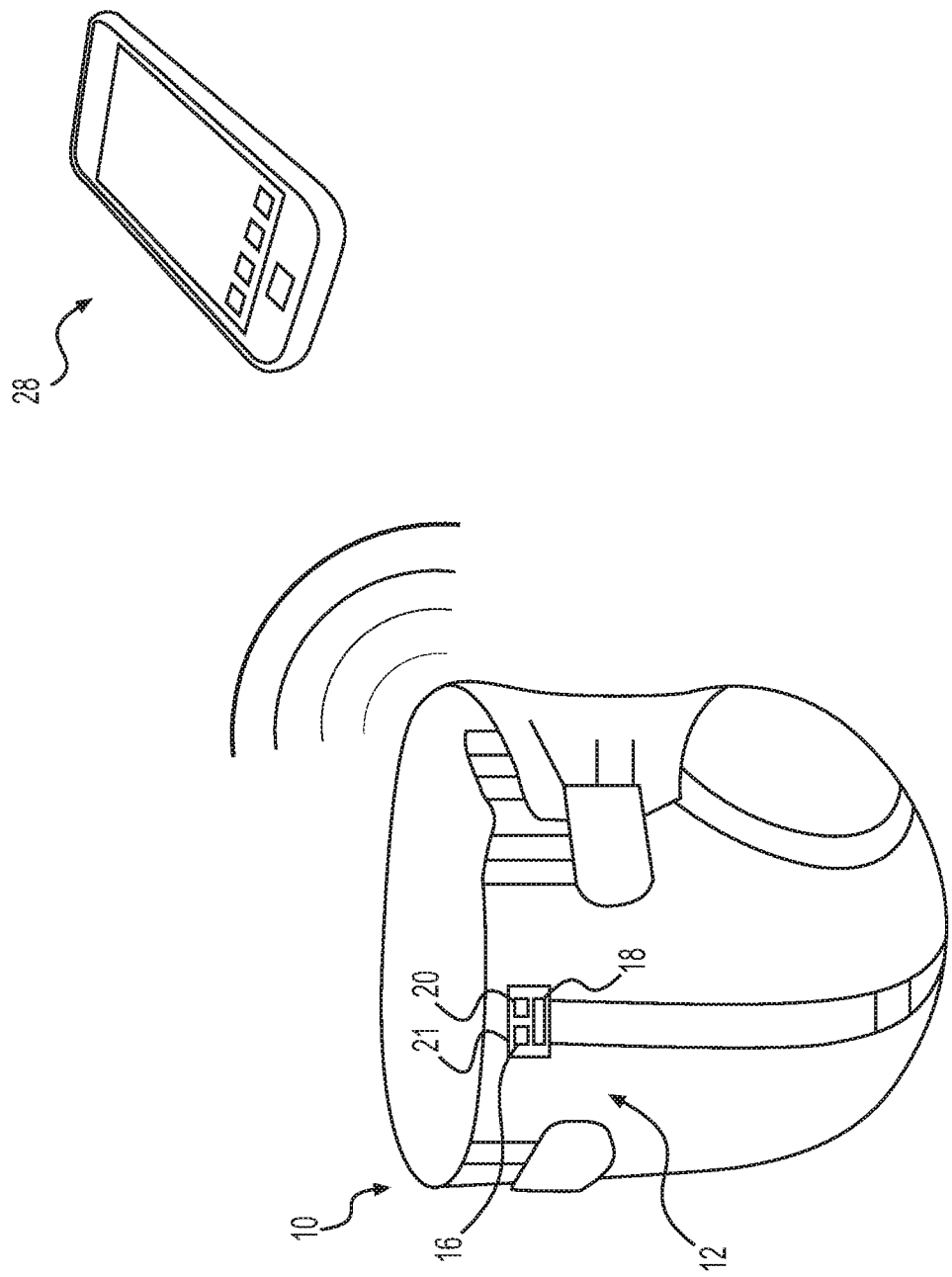
FIG. 3 is a schematic of the diaper and diaper sensor of FIG. 1.

As shown in FIG. 3, transmitter 16 may be any suitable transmitter configured to wirelessly transmit a signal or a plurality of signals to a remote device (e.g., a smart phone, a smart watch, a computer, etc.) using one or more wireless communication methods. These one or more signals transmitted be transmitter 16 may be received by a remote device 28 or other device, which may be recorded and the event(s) (e.g., defecation and/or urination) may be catalogued. In addition, remote device 28 may generate an alert. The alert may be auditory (e.g., an alarm), visual (e.g., image or message), or a combination of auditory and visual. In some embodiments, transmitter 16 may be a transceiver designed to transmit and receive signal, including for example, data, instructions, or the like.

In some embodiments, transmitter 16 may be a low-energy radio transponder. For example, transmitter 16 may be a BLUETOOTH Low Energy (BLE) transponder, such as a BLUETOOTH Smart or BLUETOOTH 4.0. Other protocols are also usable such as passive WiFi, ZIGBEE, 6LoW-PAN or Z-Wave. It is also contemplated that transmitter 16 may utilize the internet of things (IoT) to communicate. It is also contemplated that transmitter 16 may utilize a variety of protocol standards to communicate, including for example, message queue telemetry transport (MQTT), extensible messaging and presence protocol (XMPP), data distribution service (DDS), advance message queuing protocol (AMQP), or the like. It is contemplated that a facility (e.g., a hospital, day care, nursery, etc.) may be setup to support communication over one or more of these protocols in order to facilitate communication from one or more transmitters 16 simultaneously.

In illustrative embodiments of the present disclosure, transmitter 16 can be activated when feces or urine is detected, and is programmed to transmit the contents of the package (i.e., the signal) for a period of time to remote device 28 or other device enabled to receive the signals from transmitter 16. In some embodiments, remote device 28 can be detected by transmitter 16 when it comes in range and opens communication, using for example Proximity Beacon application program interface (API) and Eddystone protocol available from Google. As will be appreciated from this disclosure, other communication protocols may be utilized. Communication between transmitter 16 and remote device 28 may be such that the connection does not require activation or syncing by the caregiver each time. Instead, in some embodiments the connection between transmitter 16 and remote device 28 may be made automatically once remote device 28 goes through an initial setup, which will configured remote device 28 to receive signals transmitted by transmitter 16 or a plurality of transmitters 16. For example, in some embodiments a caregiver caring for multiple babies may receive signals via remote device 28 from multiple transmitters 16 each associated with a different diaper 10 on a different baby.

When transmitter 16 as disclosed herein transmits data, the data can be sent in advertising packets through one or more wireless advertising channels. The transmission of advertising packets may take place periodically during advertising events. Within an advertising event, transmitter 16 can sequentially use each advertising channel for packet transmission. In some embodiments, remote device 28 may scan these advertising channels for the presence of advertising packets from transmitter 16. In some embodiments, the transmissions from transmitter 16 to remote device 28 can also take place over a bidirectional data communication link. The creation of such a connection can include transmitter 16 announcing over advertising channels that it is a connectable device, while remote device 28 listens for such advertisements. When remote device 28 finds transmitter 16, it may transmit a connection request message to transmitter 16, which establishes a point-to-point connection between the two. The packets for this connection can be identified by an access code for security. In other embodiments, transmitter 16 can send advertising packets without connecting to remote device 28. In this case, the transmissions are undirected and broadcast to all devices in a vicinity.

In some embodiments, transmitter 16 can broadcast encrypted data. For example, diaper sensor 12 may include an encryption key, such as a QR or bar code on diaper 10. Remote device 28, or other device, can be used to scan the code (e.g., using an on-board camera), input the code, or otherwise receive the encryption key, and use the key to receive encrypted data from transmitter 16. In this way, only authorized devices may receive broadcasts from transmitter 16, which can increase security, for example when undirected transmissions are used.

In some embodiments, transmitter 16 may broadcast data not just when feces or urine is detected, but instead transmitter 16 may transmit a clean signal that may be received by remote device 28 when diaper 10 is clean. For example, transmitter 16 may transmit a clean signal that may be terminated when transmitter 16 begins transmitting the feces signal or the urine signal. In some embodiments, transmitter 16 may transmit an initial signal when diaper 10 is put on the baby so remote device 28 can record and catalogue diaper changes and verify communication between transmitter 16 and remote device 28 is working. In some embodiments, transmitter 16 may broadcast a final signal when diaper 10 is removed from the baby and discarded so it can be recorded and catalogued. In some embodiments, control circuit 18 and transmitter 16 may be instructed by control circuit 18 to only transmit a signal when feces is determined to be present or only when urine is determined to be present.

As described herein, remote device 28 may be a smart phone, a smart watch, or other programmable user interface device with a mobile operating system. Remote device 28 may run or execute a programmable application ("the app") designed to interface with diaper sensor 12 and transmitter 16 of one or more diapers 10. The app may be downloadable to remote device 28 via the internet or an app store, for example, the PLAY STORE operated by Google.

Figure 4:
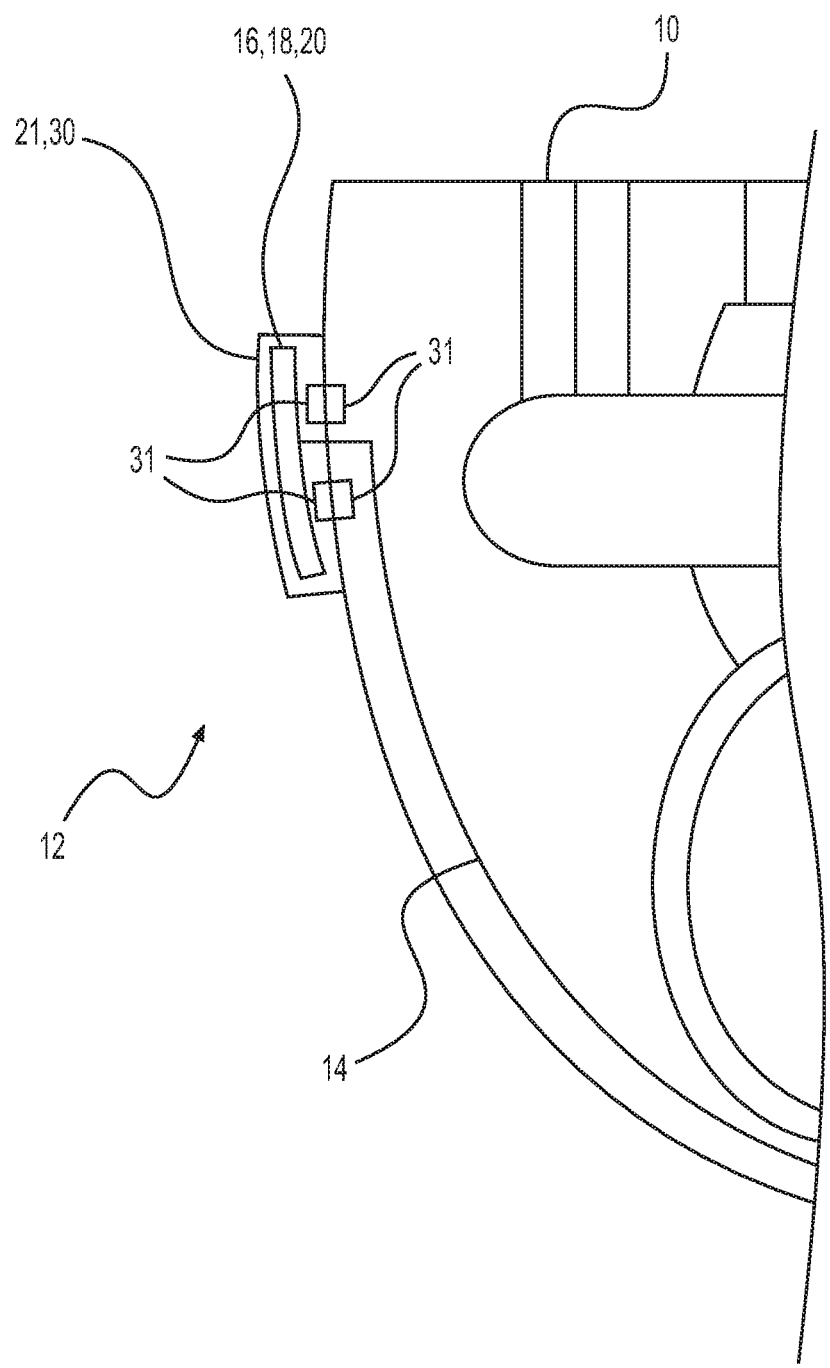
FIG. 4 is a side view schematic of a diaper sensor, according to an exemplary embodiment.

In some embodiments, diaper sensor 12 may be integrated into diaper 10, such that diaper sensor 12 is manufactured into diaper 10. In other embodiments, a portion of diaper sensor 12 may be integrated or manufactured as part of diaper 10 while another portion of diaper sensor 12 may be external and releaseably attachable to diaper sensor 12. For example, in some embodiments as shown in FIG. 4, conductive elements 14 may be integrated into diaper 10 during manufacturing while electronics module 21, including transmitter 16, control circuit 18, and power source 20 may be located in a housing 30 external to diaper 10. Housing 30 may be releaseably attachable to diaper 10 enabling it to be reused with multiple diapers. Housing 30 may be attachable to diaper 10 using a plurality of magnets 31, which may be positioned in diaper 10 and housing 30. Magnets 31 may be positioned to align the connection between control circuit 18 and conductive elements 14, as shown in FIG. 4.

In some embodiments, diaper sensor 12 may also include a moisture sensor 32. The location of temperature sensor may vary. For example, in some embodiments, moisture sensor may be positioned in absorbent region 22 and may be connected to control circuit 18 and power source 20, as shown in FIG. 1. In some embodiments, moisture sensor 32 may be configured to initiate measurement of the conductivity between conductive elements 14 when the presence of moisture has been detected. Moisture sensor may be an extremely low power sensor, which acts as a wakeup for control circuit 18 to begin measuring conductivity once moisture from either a poop or pee is first detected. Delaying measurement of the conductivity until some initial moisture is detected can preserve battery life and extend the operational life of diaper sensor 12 and/or decreases the size and/or power capacity of power source 20.

In some embodiments, moisture sensor 32 may include a dissolvable resistor operatively connected between power source 20 and a reset input of control circuit 18 that may hibernate control circuit 18 and conserve battery life. The dissolvable resistor may be configured to transition from a resistance less than about 100 kOhm when dry to greater than about 10 MOhm when dissolved by moisture. The resistance values for the dry state and the dissolved state may vary depending on the design of control circuit 18 and power source 20.

In some embodiments, diaper sensor 12 may also include a temperature sensor 34 operatively connected to control circuit 18, as shown in FIG. 1. The location of temperature sensor may vary. For example, in some embodiments, temperature sensor 34 may be positioned in absorbent region 22 so that it may measure a temperature, a temperature change, and/or a thermal mass within absorbent region 22 and output a temperature signal. In some embodiments, control circuit 18 may use the temperature signal to help differentiate between feces and urine. In some embodiments, control circuit 18 may use the temperature signal to initiate measurement of the conductivity between conductive elements 14. In other words, the temperature signal from temperature sensor 34 may be used to wake up control circuit 18.

In some embodiments, temperature sensor 34 may be used to detect when diaper 10 is put on a baby based on the temperature change caused by the initial contact with a baby's body. For these embodiments, control circuit 18 may be design to transmit a signal to remote device 28 indicating diaper 10 has been put on.

In some embodiments, diaper sensor 12 may also include an accelerometer 36 operatively connect to control circuit 18, as shown in FIG. 1. In some embodiments accelerometer 36 may be mounted to control circuit 18 or in some embodiments accelerometer 36 may be positioned in absorbent region 22. Accelerometer 36 may be designed to output a positioning signal indicative of the position of diaper 10. For example, accelerometer 36 may be designed to detect changes in the positioning of diaper 10 in response to feces or urine. In some embodiments, control circuit 18 may use the positioning signal from accelerometer 36 to help differentiate between the presence of feces and urine. In some embodiments, control circuit 18 may use the positioning signal from accelerometer 36 to initiate measurement of the conductivity between conductive elements 14 by control circuit 18. In other words, accelerometer may be used to wake up control circuit 18.

In some embodiments, accelerometer 36 may be used to detect when diaper 10 is put on a baby based on movement and positioning of diaper 10. For these embodiments, control circuit 18 may be design to transmit a signal to remote device 28 indicating diaper 10 has been put on.

In some embodiments, control circuit 18 may use the temperature signal and/or the positioning signal to initiate measurement of the conductivity between conductive elements 14 by control circuit 18. In some embodiments, control circuit 18 may use the temperature signal and/or the positioning signal in combination with the impedance measurement to determine whether there is feces or urine in diaper 10.

Figure 5:
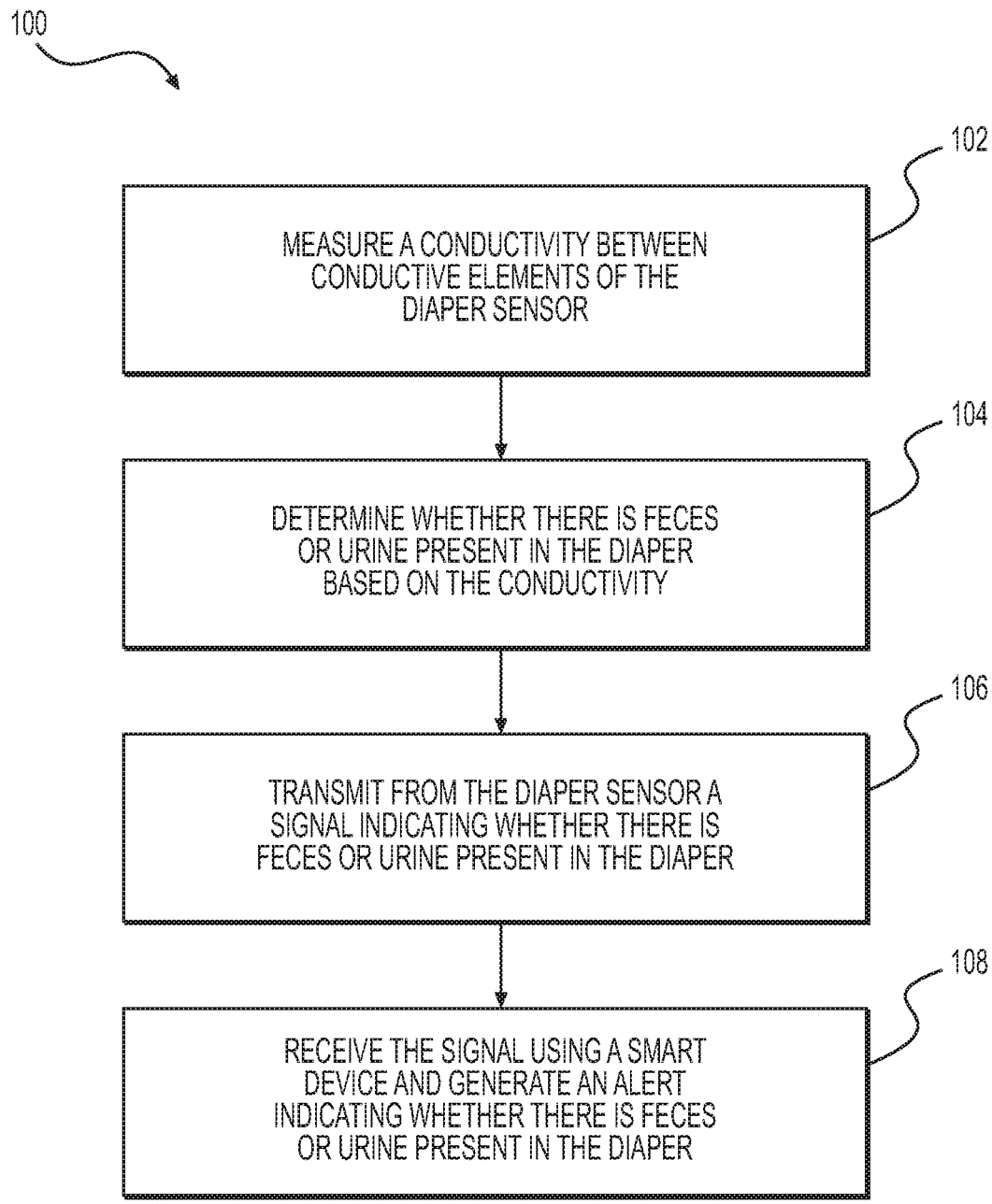
FIG. 5 is a flow chart illustrating a method of monitoring a diaper, according to an exemplary embodiment.

Diaper sensor 12 may be utilized for a variety of methods of monitoring a diaper. For example, a method 100 will be explained with reference to FIG. 5. FIG. 5 is a flow chart showing steps of method 100. Method 100 may begin at step 102 by measuring a conductivity between a pair of conductive elements 14 of a diaper sensor 12, wherein the pair of conductive elements 14 are positioned within an absorbent region of a diaper 10. At step 104, method 100 may include determining whether there is feces or urine present in diaper 10 based on the conductivity. In some embodiments, method 100 may include determining whether there is feces or urine present in diaper based on the impedance determined based on the conductivity. At step 106, method 100 may include transmitting from diaper sensor 12 a signal indicative of whether there is feces or urine present in diaper 10. At step 108, method 100 may include receiving the signal using remote device 28 (e.g., smart phone) and generating an alert indicating whether there is feces or urine present in diaper 10.

Optionally, method 100 may include initiating the measuring of the conductivity after moisture sensor 32 detects the initial presence of moisture in diaper 10. Optionally, method 100 may also include monitoring a temperature of diaper 10 and using the detection of a temperature change to initiate measurement of the conductivity by the control circuit. Optionally, method 100 may also include monitoring a temperature of diaper 10 and using a temperature change to help control circuit 18 differentiate between feces and urine. Optionally, method 100 may also include generating a positioning signal and using the positioning signal to determine when to initiate measurement of the conductivity by control circuit 18 or help control circuit 18 differentiate between feces and urine. Optionally, method 100 may also include attaching housing 30 containing transmitter 16, control circuit 18, and power source 20 to diaper 10 and positioning housing 30 to align a connection between conductive elements 14 and control circuit 18.

The foregoing description has been presented for purposes of illustration. It is not exhaustive and is not limited to precise forms or embodiments disclosed. Modifications and adaptations of the embodiments will be apparent from consideration of the specification and practice of the disclosed embodiments.

Although described in relation to use with a baby, it is understood that the diaper sensor of the present disclosure described herein may be employed with other individuals besides and may also be employed with animals.

Moreover, while illustrative embodiments have been described herein, the scope includes any and all embodiments having equivalent elements, modifications, omissions, combinations (e.g., of aspects across various embodiments), adaptations and/or alterations based on the present disclosure. The elements in the claims are to be interpreted broadly based on the language employed in the claims and not limited to examples described in the present specification or during the prosecution of the application, which examples are to be construed as nonexclusive. Further, the steps of the disclosed methods can be modified in any manner, including reordering steps and/or inserting or deleting steps.

The features and advantages of the disclosure are apparent from the detailed specification, and thus, it is intended that the appended claims cover all systems and methods falling within the true spirit and scope of the disclosure. As used herein, the indefinite articles "a" and "an" mean "one or more." Similarly, the use of a plural term does not necessarily denote a plurality unless it is unambiguous in the given context. For example, the term feces as used herein is intended to denote either the singular or plural form. Words such as "and" or "or" mean "and/or" unless specifically directed otherwise. Further, since numerous modifications and variations will readily occur from studying the present disclosure, it is not desired to limit the disclosure to the exact construction and operation illustrated and described, and accordingly, all suitable modifications and equivalents may be resorted to, falling within the scope of the disclosure.

The term "about" as used herein means within an acceptable error range from the particular value as determined by one of ordinary skill in the art, which will dependent in part on how the value is measured or determined, e.g., the limitations of the measurement system. For example, "about" can mean within one or more than one standard deviation per the practice in the art. Alternatively, "about" can mean a range of up to 20%, such as up to 10%, up to 5%, and up to 1% of a given value.

Computer programs, program modules, and code based on the written description of this specification, such as those used by the microcontrollers, are readily within the purview of a software developer. The computer programs, program modules, or code can be created using a variety of programming techniques. For example, they can be designed in or by means of Java, C, C++, assembly language, or any such programming languages. One or more of such programs, modules, or code can be integrated into a device system or existing communications software. The programs, modules, or code can also be implemented or replicated as firmware or circuit logic.

Other embodiments will be apparent from consideration of the specification and practice of the embodiments disclosed herein. It is intended that the specification and examples be considered as example only, with a true scope and spirit of the disclosed embodiments being indicated by the following claims.

In an embodiment, a diaper sensor for detecting and differentiating feces and urine in a diaper, includes at least one pair of conductive elements positioned within an absorbent region of the diaper, a transmitter, a control circuit operatively connected to the at least one pair of conductive elements and the transmitter, and a power source operatively connected to the control circuit. The control circuit can measure a conductivity between the at least one pair of conductive elements. The control circuit can further determine whether there is feces or urine present in the diaper using the conductivity. The control circuit can further transmit via the transmitter a signal indicative of whether there is feces or urine present in the diaper.

In an embodiment, the pair of conductive elements of the diaper sensor includes conductive fibers that are woven into the absorbent region. In a further embodiment, the conductive fibers are carbon fibers and are woven to form an inter-digitated array.

In an embodiment, the transmitter can use at least one of BLUETOOTH Low Energy, BLUETOOTH Smart, BLUETOOTH 4.0, WiFi, ZIGBEE, 6LoWPAN, and Z-Wave to transmit the signal.

In an embodiment, the transmitter, control circuit, and power source are integrated into a diaper.

In an embodiment, the diaper sensor includes a moisture sensor that initiates measurement of the conductivity when moisture is present.

In an embodiment, the moisture sensor can include a resistor that is moisture dissolvable. The resistor can be operatively connected to the control circuit so that when the resistor dissolves as a result of moisture, the control circuit begins measuring the conductivity between the conductive elements.

In an embodiment, the transmitter, the control circuit, and the power source are located in a housing external to the diaper and the housing is releaseably attachable to a diaper.

In an embodiment, the diaper sensor can include magnetic elements in the diaper and the housing. The magnetic elements can releaseably attach the housing to a diaper and can be positioned to align a connection between the control circuit and the at least one pair of conductive elements.

In an embodiment, the diaper sensor further includes a temperature sensor operatively connected to the control circuit. The temperature sensor can measure a thermal mass of the diaper and the control circuit uses the thermal mass to help differentiate between feces and urine.

In an embodiment, the diaper sensor includes an accelerometer operatively connected to the control circuit. The accelerometer outputs a positioning signal indicative of the positioning of a diaper. The control circuit uses the positioning signal to help differentiate between feces and urine.

In an embodiment, the diaper sensor further includes an accelerometer operatively connected to the control circuit. The accelerometer outputs a positioning signal indicative of the positioning of a diaper, and the control circuits use the positioning signal to initiate measurement of the conductivity by the control circuit.

In an embodiment, a method of monitoring a diaper using a diaper sensor includes measuring a conductivity between a pair of conductive elements of a diaper sensor. The pair of conductive elements are positioned within an absorbent region of a diaper. The method further includes determining whether there is feces or urine present in the diaper based on the conductivity. The method further includes transmitting from the diaper sensor a signal indicative of whether there is feces or urine present in the diaper.

In an embodiment, the method further includes initiating measuring of the conductivity after a moisture sensor integrated into a diaper detects the presence of moisture in the diaper.

In an embodiment, the method further includes monitoring a temperature of the diaper and using a temperature change to determine when to initiate measurement of the conductivity by the control circuit or help the control circuit determine whether there is feces or urine present.

In an embodiment, the method further includes generating a positioning signal for the diaper and using the positioning signal to determine when to initiate measurement of the conductivity by the control circuit or using the positioning signal to help differentiate between feces and urine.

In an embodiment, the method further includes receiving the signal using a smart phone and generating an alert indicating whether there is feces or urine present in a diaper based on the signal.

In an embodiment, the method further includes attaching a housing of the diaper sensor to a diaper, the housing contains a transmitter, a control circuit, and a power source of the diaper sensor.

In an embodiment, a diaper sensor for detecting and differentiating feces and urine in a diaper includes at least one pair of conductive elements positioned within an absorbent region of the diaper, a transmitter; a control circuit operatively connected to the at least one pair of conductive elements and the transmitter; and a power source operatively connected to the control circuit. The control circuit measures the conductivity between the at least one pair of conductive elements to determine an impedance. The control circuit determines whether there is feces or urine present in the diaper based on the impedance. The control circuit transmits via the transmitter a signal indicative of whether there is feces or urine present in the diaper.

The invention claimed is:
1. A diaper sensor for detecting feces and urine in a diaper, comprising:
    at least one pair of conductive elements positioned within an absorbent region of the diaper;
    a transmitter configured to transmit a signal indicating a presence of feces or urine;
    a moisture sensor that comprises a dissolvable resistor; and
    a control circuit operatively connected to the at least one pair of conductive elements and the transmitter,
    wherein the control circuit is operatively connected to a power source and is configured to perform operations comprising:
        detecting that the dissolvable resistor has dissolved;

measuring a conductivity between the at least one pair of conductive elements that are positioned in the absorbent region of the diaper; and determining a presence of feces or urine based on the measurement of conductivity.

2. The diaper sensor of claim 1, wherein the at least one pair of conductive elements includes a plurality of conductive fibers woven into the absorbent region.

3. The diaper sensor of claim 2, wherein the plurality of conductive fibers are carbon fibers and are woven to form an inter-digitated array.

4. The diaper sensor of claim 1, wherein the transmitter uses at least one of BLUETOOTH Low Energy, BLUETOOTH Smart, BLUETOOTH 4.0, WiFi, ZIGBEE, 6LoWPAN, and Z-Wave to transmit the signal.

5. The diaper sensor of claim 1, wherein the transmitter, the control circuit, and the power source are integrated into the diaper.

6. The diaper sensor of claim 1, wherein the transmitter, the control circuit, and the power source are located in a housing external to the diaper and the housing is releaseably attachable to the diaper.

7. The diaper sensor of claim 6, further comprising magnetic elements positioned in the diaper and the housing, wherein the magnetic elements releaseably attach the housing to the diaper, and wherein the magnetic elements are positioned to align a connection between the control circuit and the at least one pair of conductive elements.

8. The diaper sensor of claim 1, further comprising a temperature sensor operatively connected to the control circuit, wherein the temperature sensor measures a thermal mass of the diaper and wherein obtaining the measurement of conductivity further comprises:

receiving a temperature measurement from the temperature sensor; and initiating the measurement of the conductivity based on the temperature measurement.

9. The diaper sensor of claim 1, further comprising a temperature sensor operatively connected to the control circuit, wherein the temperature sensor measures a thermal mass of the diaper and the control circuit uses the thermal mass to determine when to initiate the measurement of the conductivity by the control circuit.

10. The diaper sensor of claim 1, further comprising an accelerometer operatively connected to the control circuit, wherein the accelerometer outputs an additional signal indicative of a positioning of the diaper, and the operations further comprise:

receiving signal from the accelerometer, wherein initiating measurement of conductivity is based on the additional signal.

11. The diaper sensor of claim 1, wherein the measurement of conductivity is between 1 milli-Siemen per centimeter and 100 milli-Siemens per centimeter.

12. A method of monitoring a diaper using a diaper sensor, the method comprising:

detecting, at a control circuit of a diaper sensor, that a dissolvable resistor has dissolved;

measuring a conductivity between a pair of conductive elements in a diaper;

determining, at the control circuit, a presence of feces or urine based on the measurement of conductivity; and causing a transmitter to transmit a signal indicative of the presence.

13. The method of claim 12, wherein measuring of conductivity comprises:

receiving a positioning signal from an accelerometer, wherein initiating measurement of conductivity is based on the positioning signal.

14. The method of claim 12, further comprising attaching a housing of the diaper sensor to the diaper, the housing containing the transmitter, the control circuit, and a power source of the diaper sensor.

15. A diaper sensor for differentiating feces and urine in a diaper, comprising:

a pair of conductive elements positioned within an absorbent region of a diaper;

a power source;

a transmitter;

a dissolvable resistor;

a control circuit operatively connected to the conductive elements that are positioned with an absorbent region of a diaper and to the transmitter, wherein the control circuit is configured to perform operations comprising:

detecting that the dissolvable resistor has dissolved;

measuring a conductivity between the conductive elements;

determining a presence of moisture based on the conductivity;

causing the power source to apply a signal at a particular frequency to the pair of conductive elements;

measuring a conductivity between the pair of conductive elements to determine an impedance;

determining, based on the impedance being greater than a first threshold but less than a second threshold, that feces are present in the diaper, wherein the first and second thresholds are determined based on the particular frequency of the signal; and transmitting via the transmitter a signal indicative of whether feces or urine is present in the diaper.

* * * * *